(12) United States Patent
Stemmer

(10) Patent No.: US 9,476,958 B2
(45) Date of Patent: Oct. 25, 2016

(54) METHOD TO DETERMINE THE ACTUAL FLIP ANGLE AND METHOD TO ADJUST THE TRANSMITTER VOLTAGE IN A MAGNETIC RESONANCE APPARATUS

(75) Inventor: Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 693 days.

(21) Appl. No.: 13/422,227

(22) Filed: Mar. 16, 2012

(65) Prior Publication Data
US 2012/0235684 A1 Sep. 20, 2012

(30) Foreign Application Priority Data

Mar. 16, 2011 (DE) .......................... 10 2011 005 649

(51) Int. Cl.
| | | |
|---|---|---|
| G01R 33/48 | (2006.01) | |
| G01R 33/34 | (2006.01) | |
| G01R 33/563 | (2006.01) | |
| A61B 5/055 | (2006.01) | |
| G01R 33/58 | (2006.01) | |

(52) U.S. Cl.
CPC ......... *G01R 33/56383* (2013.01); *A61B 5/055* (2013.01); *G01R 33/586* (2013.01)

(58) Field of Classification Search
CPC ............ A61B 5/055; G01R 33/56383; G01R 33/586; G01R 33/56375
USPC ............................ 324/300–322; 600/407–422
See application file for complete search history.

(56) References Cited

U.S. PATENT DOCUMENTS

| | | |
|---|---|---|
| 4,814,708 A | 3/1989 | Van Der Meulen et al. |
| 4,983,921 A | 1/1991 | Kramer et al. |
| 5,853,365 A | 12/1998 | Yamagata |
| 7,110,805 B2 | 9/2006 | Machida |
| 7,145,338 B2 | 12/2006 | Campagna et al. |
| 7,227,356 B1 * | 6/2007 | Hariharan et al. ............ 324/307 |
| 2002/0021127 A1 * | 2/2002 | Hennig ......................... 324/307 |
| 2002/0115929 A1 * | 8/2002 | Machida ....................... 600/410 |
| 2004/0051527 A1 * | 3/2004 | Mugler, III et al. .......... 324/309 |
| 2004/0189297 A1 * | 9/2004 | Bock et al. ................... 324/307 |
| 2007/0075707 A1 | 4/2007 | Kawai et al. |
| 2007/0145975 A1 | 6/2007 | Feiweier et al. |
| 2008/0319301 A1 * | 12/2008 | Busse ........................... 600/410 |
| 2009/0134871 A1 | 5/2009 | Yui |

(Continued)

OTHER PUBLICATIONS

Shankaranarayanan et al., "Continuous Adjustment of Calibration Values for Improved Image Quality in Continuously Moving Table Imaging," Proc. Intl. Soc. Mag. Reson. Med. 11 (2004), p. 103.

(Continued)

*Primary Examiner* — Melissa Koval
*Assistant Examiner* — Rishi Patel
(74) *Attorney, Agent, or Firm* — Schiff Hardin LLP

(57) ABSTRACT

In a method to determine the actual flip angle in magnetic resonance tomography with continuous table feed, at least one echo signal is generated by a pulse sequence from which an actual flip angle is produced with at least one RF pulse of the sequence, and a gradient scheme is used in the direction of the continuous travel of the examination subject, the gradient scheme being designed such that its first moment disappears at the points in time of each echo signals used for the determination of the flip angle. Such a pulse sequence is also used in a method for adjustment of the transmitter voltage for RF pulses given continuous travel of the examination subject in a magnetic resonance apparatus.

12 Claims, 6 Drawing Sheets

(56) References Cited

U.S. PATENT DOCUMENTS

| | | | |
|---|---|---|---|
| 2009/0177078 A1* | 7/2009 | Takizawa | A61B 5/055 600/415 |
| 2009/0219020 A1* | 9/2009 | Kurokawa | G01R 33/56375 324/309 |
| 2009/0251142 A1 | 10/2009 | Taniguchi et al. | |
| 2010/0045288 A1 | 2/2010 | Horger et al. | |
| 2010/0189328 A1 | 7/2010 | Boernert et al. | |
| 2010/0280357 A1 | 11/2010 | Bi et al. | |

OTHER PUBLICATIONS van der Meulen et al., "A Novel Method for Rapid Pulse Angle Optimisation," Proceedings of the 5th Annual Meeting of SMRM (1986), pp. 1129-1130.

Bernstein et al., "Minimizing TE in Moment-nulled or Flow-encoded Two- and Three-dimensional Gradient-Echo Imaging," Journal of Magnetic Resonance Imaging, vol. 2, Issue 5 (1992), pp. 583-588.

Koken et al., "Towards Automatic Patient Positioning and Scan Planning Using Continuously Moving Table MR Imaging," Magnetic Resonance in Medicine, vol. 62 (2009), pp. 1067-1072.

Perman et al., "A Method for Correctly Setting the rf Flip Angle," Magnetic Resonance in Medicine, vol. 9 (1989), pp. 16-24.

Carlson et al., "Rapid Radiofrequency Calibration in MRI," Magnetic Resonance in Medicine, vol. 15 (1990), pp. 438-445.

Stemmer et al., "Robust Transmitter Calibration during Continuous Table Movement," Proc. Intl. Soc. Mag. Reson. Med., vol. 19 (2011), p. 2924.

Bernstein et al., "Handbook of MRI Pulse Sequences," Chapter 10.4, Gradient Moment Nulling, pp. 331-349 (2004).

* cited by examiner

METHOD TO DETERMINE THE ACTUAL FLIP ANGLE AND METHOD TO ADJUST THE TRANSMITTER VOLTAGE IN A MAGNETIC RESONANCE APPARATUS

BACKGROUND OF THE INVENTION

1. Field of the Invention

The invention concerns a method to determine the actual flip angle of at least one RF pulse of a pulse sequence during continuous travel of the examination subject in a magnetic resonance apparatus, a method to adjust the transmitter voltage for RF pulses during continuous travel of the examination subject in a magnetic resonance apparatus, and a magnetic resonance apparatus to implement such methods, as well as a non-transitory electronically readable data storage medium that causes a processor, in which the medium is loaded, to implement such methods.

2. Description of the Prior Art

Magnetic resonance (MR) tomography is an imaging method that is used in materials research, pharmaceutical development, and primarily in medical diagnostics. In magnetic resonance tomography, the examination subject is exposed to a homogeneous, static basic magnetic field B0. The nuclear spins (abbreviated as spins) of the examination subject align parallel to the field. To generate measurement signals (in particular images), this steady state is initially disrupted by the radiation of radio-frequency pulses (abbreviated as: RF pulse). The field emitted during the return of the pins to the steady state is spatially coded by the switching of gradient fields, and the signals corresponding to this field received with one or more reception coils. An RF pulse generates a field that is designated as the B1 field, which is amplitude-modulated and oscillates with a carrier frequency. The B1 field is oriented perpendicularly to the B0 field. An RF pulses is characterized by its bandwidth δf, its time duration T, and the time curve of its envelope B1(t). The magnetization of spins whose resonance frequency lies within the bandwidth of the RF pulse is flipped out of the steady state at the end of the RF pulse by the angle $$\alpha = \gamma \int_{t_0}^{t_0+T} B_1(t) \, dt \quad (1)$$

wherein t0 is the activation time of the RF pulse, and the gyromagnetic ratio γ is a physical constant that depends on the excited nucleus. For protons, its value is γ=2π 42.57 MHz/T.

The angle α (also called a tilt angle or flip angle) significantly affects contrast and signal strength of the images calculated from the received signal. If the flip angle required by the imaging sequence is not achieved, or if the rotation exceeds this flip angle, this leads to contrast and signal losses, the severity of which depends on the sequence technique that is used.

The B1 field generated by an RF pulse depends not only on the controllable output voltage of the radio-frequency amplifier (in turn, the current through the transmission coil) but also on a load that is dependent on the examination subject, for example a patient-specific load given examinations of patients. Therefore, for a precise determination of the flip angle it is necessary to determine the output voltage of the radio-frequency amplifier (which generates a defined B1 field for a normalized reference RF pulse, and therefore a desired flip angle α of the magnetization) for each examination subject and for every position of the examination subject in the basic magnetic field, for example in what is known as a "transmitter adjustment". The result of a "transmitter adjustment" is also designated in the following as a reference transmitter voltage, or abbreviated as a reference voltage. If the examination subject is a patient, such a determination should take place for each patient, and ideally for each position of the patient bed (and therefore of the patient) that will be adopted for the diagnostic measurement (data acquisition) of the examination. In the following, a patient is discussed as an examination subject. The information analogously applies to other examination subjects.

If the duration of an RF pulse or their envelope B1(t) of an RF pulse differs from the duration or the envelope of the reference RF pulse, the output voltage of the radio-frequency amplifier for this RF pulse is scaled relative to the reference voltage according to Equation (1) above.

The time expended for the transmitter adjustment (and possibly other adjustment measurements that must be implemented specific to the patient to ensure a desired image quality) is additive to the total examination duration, and therefore adds to the cost of the MR examination and the stress to which the patient is exposed by the examination.

If measurement now takes place in an examination with varying positions of the patient bed, the adjustment measurements should optimally be implemented repeatedly for each individual position. For this purpose, the respective individual positions would need to be occupied in succession and the patient bed would need to be halted at each position in order for the adjustment measurement to take place, which is extremely time-consuming (and therefore unattractive). For example, this is the case in examinations known as multi-step whole-body or partial-body examinations, and in particular in examinations in which measurement takes place during continuous feed of the patient bed (known as "move during scan" (MDS), "continuously moving table MRI" (CMT) and "syngo TimCT" (Siemens proprietary terminology)).

As used herein "adjustment measurements" encompasses all measurements that are implemented specific to the patient and possibly specific to the bed position in order to be able to produce a fine tuning of the MR system to the specific load. In addition to the transmitter adjustment that is discussed above, they normally additionally may include a tuning of the coils ("coil tuning") in order to compensate for the influence of the patient on the inductance, the capacitance and the resistance of the oscillating circuit used for reception, a frequency adjustment in order to adapt the RF carrier frequency or center frequency to the resonance frequency of the nucleus under consideration (most often free water); and a "shim adjustment" in order to reestablish the homogeneity of the magnetic field (which homogeneity is disrupted by the person to be examined or by the examination subject to be examined).

In numerous publications about MR measurements that are implemented during continuous travel of the patient bed, patient-specific adjustment measurements are omitted entirely. Instead of this, patient-independent system values or empirically determined experimental values for the load-dependent adjustment values are used, for example, and image quality limitations are accepted as a result. One exception is the work by A. Shankaranarayanan and J. Brittain, "Continuous Adjustment of Calibration Values for Improved Image Quality in Continuously Moving Table Imaging", Proc. Intl. Soc. Mag. Reson. Med. 11 (2004), #103. The authors describe a modification of the adjustment values during the continuous travel. The adjustment values that are thereby used are determined before the actual measurement, at 16 stations distributed over the complete body in what is known as a "prescan" given a stationary bed.

Known adjustment methods with stationary patient beds are frequently implemented iteratively, meaning that a start voltage is initially selected and the flip angle that is achieved with this is determined with the use of the method. If the flip angle deviates significantly from the desired flip angle of the reference RF pulse (for example 180° or 90°), a new transmitter voltage is extrapolated using the flip angle measured in the preceding iteration step and the desired flip angle, and the method is repeated with the transmitter voltage that is determined in such a manner. The iteration ends when the deviation between measured flip angle and desired flip angle falls below a determined threshold.

A transmitter adjustment during continuous feed of the patient bed is already known from U.S. Pat. No. 7,145,338 B2, whereby the problem described above, namely the need to occupy all individual positions for the adjustment measurements successively and to halt the patient bed for the adjustment measurement, can be circumvented.

Such a method can be used in magnetic resonance apparatuses commercially available from Siemens Healthcare for MR examinations in which measurement takes place during continuous feed of the patient bed. The method is not iteratively as under stationary conditions; rather, the transmitter voltage extrapolated with the aid of the start voltage, the desired flip angle and the measured flip angle is set equal to the transmitter reference voltage. The reason is that, due to the continuous travel, the load would change between the individual iteration steps (and thus a convergence cannot be assumed). Further the time duration per adjustment measurement must be constant in order to achieve a predetermined spatial resolution of the transmitter reference voltage as a function of the bed position given a constant speed of the patient bed.

A known method for transmitter adjustment determines the output voltage of the radio-frequency amplifier that is necessary to realize the reference RF pulse by means of a sequence that has three RF pulses, which sequence is shown as an example in FIG. 1.

This method is based on a method that was first proposed by Peter van der Meulen and Gerrit H. van Yperen 1986 at the 5th Annual Meeting of SMRM (Peter van der Meulen and Gerrit H. van Yperen in "A novel method for rapid pulse angle optimization", Proceedings of the 5th Annual Meeting of SMRM 5th Annual Meeting of SMRM; (1986). p. 1129) and is described in U.S. Pat. No. 4,814,708. The method uses a pulse sequence with three RF pulses as shown in FIGS. 1 and 2 and described in the following.

If $\alpha$ is the flip angle of the first RF pulse, $\alpha 2$ is the flip angle of the second RF pulse and $\alpha 3$ is the flip angle of the third RF pulse, and if $\tau 1$ is the time interval between the first and second RF pulses and $\tau 2$ is the time interval between the second and third RF pulses, up to five echoes E1, S1, E2, E3, E4 are obtained (see FIG. 1), in particular a first spin echo E1 at time $\tau 1$ after the first RF pulse and a stimulated echo S1 at time $\tau 1$ after the third RF pulse.

The intensity of the echoes as a function of the flip angle $\alpha 1$ to $\alpha 3$, the time intervals between the RF pulses $\tau 1$ and $\tau 2$ and the relaxation times T1 and T2 of the examined tissue can simply be calculated analytically. The result for the intensity of the first spin echo is, for example:

$$I_{E1} = M_z^0 \sin(\alpha 1)\sin^2\left(\frac{\alpha 2}{2}\right)e^{-\frac{2\tau_1}{T_2}} \quad (2)$$

The intensity $I_{S1}$ of the stimulated echo amounts to:

$$I_{S1} = \frac{1}{2}M_z^0 \sin(\alpha 1)\sin(\alpha 2)\sin(\alpha 3)e^{-\frac{\tau_2}{T_1}}e^{-\frac{2\tau_1}{T_2}} \quad (3)$$

$M_z^0$ is thereby the value of the magnetization at the thermal steady state.

Since the relative value of the flip angles $\alpha 1$, $\alpha 2$, $\alpha 3$ is adjustable via the design of the RF pulses in the sequence (for example via the duration of otherwise identical RF pulses), the desired absolute value of the flip angle can be determined via the measurement of the intensities of at least two echoes. For example, Van der Meulen and van Yperen select all three flip angles to be identical ($\alpha 1 = \alpha 2 = \alpha 3 = \alpha$) and measure the intensity of the first spin echo and the intensity of the stimulated echo under a constant gradient in the z-direction, as is depicted in FIG. 2. With the aid of Equations 2 and 3, the sought absolute value of the flip angle then results from the ratio of the intensities $I_{S1}/I_{E1}$:

$$\frac{I_{S1}}{I_{E1}} = \frac{\frac{1}{2}\sin^2(\alpha)}{\sin^2\left(\frac{\alpha}{2}\right)}e^{-\frac{\tau_2}{T_1}} =$$

$$\frac{\sin^2(\alpha)}{1-\cos(\alpha)}e^{-\frac{\tau_2}{T_1}} = \frac{1-\cos^2(\alpha)}{1-\cos(\alpha)}e^{-\frac{\tau_2}{T_1}} = (1+\cos(\alpha))e^{-\frac{\tau_2}{T_1}}.$$

Also:

$$\alpha = \arccos\left(\frac{I_{S1}}{I_{E1}}e^{\frac{\tau_2}{T_1}} - 1\right) \quad (4)$$

The constant gradient $G_z$ in the z-direction (direction of the basic magnetic field B0) has multiple functions: during the RE excitation, it serves as a slice selection gradient that limits the excitation volume in the z-direction. The limitation thereby depends on the amplitude of the gradient and the bandwidth $\delta f$ of the RF pulses that are used. During the signal reception, the gradient $G_z$ serves as a readout gradient that frequency-codes the echo signals along the z-direction. After a one-dimensional, discrete, complex Fourier transformation of the two echo signals E1 and S1, a one-dimensional, complex slice profile is thus obtained along the z-direction $P_{S1}(z)$ and $P_{E1}(z)$. In Equation 4, the magnitude of the intensity of the central pixel of the respective slice profile is typically used for $I_{S1}=|P_{S1}(z_0)|$ and $I_{E1}=|P_{E1}(z_0)|$. This means that the average flip angle is determined in the center $z_0$ of the excitation volume. The term "average flip angle" is used because, due to the lacking a spatial resolution of the method along the two other spatial directions, the echo signals along these two directions are inherently complexly integrated (and therefore averaged). An average T1 value of the tissue in the projection volume is accordingly also to be used for the T1 value in Equation 4.

A modified version of the method just described for transmitter adjustment given stationary measurements is used in DE 10 2005 061 567 B3. The flip angle of the second RF pulse is thereby chosen to be twice as large as the flip angles of the first RF pulse and third RF pulse, thus $\alpha 1 = \alpha 3 = \alpha$ and $\alpha 2 = 2\alpha$. The sought flip angle $\alpha$ is determined from the following Formula 5:

$$\cos(\alpha) = \frac{P_{E1}(z_0) \cdot P_{S1}(z_0)}{|P_{E1}(z_0)|^2} e^{\frac{\tau_2}{T_1}} \quad (5)$$

Due to the complex multiplication in Formula 5, the method is thus phase-sensitive.

An additional method it to adjust the transmitter voltage given stationary measurements is described in Perman et al., "A Method for Correctly Setting the RF flip angle", MRM9: 16-24 (1989), for example. The sequence of three RF pulses to generate the echoes E1, S1, E2, E3 and E4 under a constant gradient in the z-direction that is depicted in FIG. 1 is likewise used there, but there the transmitter voltage which is required to generate 90° or, respectively, 180° RF pulses is determined not using the first echo E1 and the stimulated echo S1 but rather only using the third echo E3.

An additional method to adjust the transmitter voltage given stationary measurements is described in Carlson et al. "Rapid Radio-frequency Calibration in MRI". MRM15: 438-445 (1990). There the sequence shown in FIG. 1 to generate the echoes E1, S1, E2, E3 and E4 under a constant gradient in the z-direction is likewise used, but there the transmitter voltage is determined using the echoes S1, E2, E3 and E4 or, respectively, using the echoes S1, E2 and E4 that arise after the third RF pulse.

The described methods operate well for stationary measurements. However they simply do not deliver satisfactory results for the adjustment of the transmitter voltage given measurements with continuous feed of the patient bed.

SUMMARY OF THE INVENTION

An object of the present invention is to provide a method to determine the actual flip angle of a pulse sequence in a magnetic resonance apparatus, a method to adjust the transmitter voltage for RF pulses by means of a pulse sequence in a magnetic resonance apparatus, a magnetic resonance apparatus to implement such methods, and a non-transitory electronically readable data storage medium to implement such methods that allow load-dependent parameters to be reliably determined for a series of positions of the patient bed during continuous travel of said patient bed (and therefore of the examination subject).

The present invention is based on the following considerations:

In the following, a one-dimensional movement of a small spin ensemble that is flipped in the transversal plane at the point in time $t_0=0$ by an excitation pulse RF1 and moves with constant velocity $v_z$ along a temporally varying gradient field $G_z(t)$ is considered. The zero point of the z-axis thereby coincides with the isocenter of the gradient. If $z_0$ is the location of the spin ensemble at the time $t_0$, the location $z(t)$ at a later point in time is thus:

$$z(t) = z_0 + v_z(t-t_0).$$

The phase of the spin ensemble that is accumulated at the time t as a result of the gradient field $G_z(t)$ amounts to:

$$\varphi(t) = \gamma \int_{t_0}^{t} G_z(\tilde{t}) z(\tilde{t}) d\tilde{t} = \gamma \int_{t_0}^{t} G_z(\tilde{t})(z_0 + v_z \tilde{t}) d\tilde{t} \quad (6)$$

Equation 6 is frequently described as a function of the moment of the gradient scheme:

$$\phi(t) = \gamma m_0(t) z_0 + \gamma m_1(t) v_z, \quad (7)$$

wherein the n-th moment $m_n(t)$ of the gradient scheme is provided by:

$$m_n(t) = \int_{t_0}^{t} G_z(\tilde{t}) \tilde{t}^n d\tilde{t} \quad (8)$$

In spin echo sequences it is additionally necessary for every refocusing RF pulse to negate the sign of the phase that was accumulated before its isodelay point. The isodelay point of a symmetrical refocusing pulse thereby coincides with its center.

The accumulated phase at the point in time of the echo is of particular interest.

If the adjustment sequence from FIG. 2 is specifically considered, and if the accumulated phase of the small spin ensemble at location z(t) at the point in time $t=2\tau_1$ of the first spin echo E1 and at the point in time $t=2\tau_1+\tau_2$ of the stimulated echo S1 is calculated with the aid of Formula 7, it results that the 0th moment—and therefore the first term in Equation 7—is respectively zero at the point in time of the echoes E1 and S1.

This is immediately clear for the spin echo E1: the first spin echo E1 arises by the second RF pulse RF2 refocusing the FID of the first RF pulse RF1. The 0th moment, which accumulates between the first RF pulse RF1 and refocusing pulse RF2, has the same absolute value $G_z\tau_1$ as the 0th moment that accumulates between RF2 and spin echo E1. The algebraic sign of both contributions is inverse; the sum is thus zero. FID ("free induction decay") thereby designates the transient signal of a spin system that is induced by an individual RF pulse.

The stimulated echo S1 arises in the interaction of all three RF pulses RF1, RF2 and RF3. The first RF pulse RF1 thereby in turn operates as an excitation pulse that flips the magnetization of the spin ensemble in the transversal plane. The second RE pulse RF2 operates as what is known as a "restore pulse" upon generation of the stimulated echo, meaning that it flips a portion of the transversal magnetization back in the longitudinal direction, and this portion is then rotated again in the transversal plane by the third RF pulse RF3. This magnetization is discussed as being stored between second and third RF pulse in the longitudinal direction since, as a longitudinal magnetization, it is not affected by the gradient fields and is also subject only to the slower longitudinal T1 relaxation. Immediately after the third RF pulse RF3, the magnetization thus has the same magnitude and the opposite sign as just before the second RF pulse RF2. The 0th moment that is accumulated between the third RF pulse RF3 and the stimulated echo S1 thus in turn cancels out the moment accumulated between the first and second RF pulse.

At the first moments it appears differently since here the time is not entered linearly but rather quadratically:

At the point in time $t=2\tau_1$ of the first spin echo E1, with the aid of Formula 8 the following first moment is obtained:

$$\begin{aligned} m_1(2\tau_1) &= -\int_0^{\tau_1} G_z \tilde{t} d\tilde{t} + \int_{\tau_1}^{2\tau_1} G_z \tilde{t} d\tilde{t} \\ &= -\frac{1}{2} G_z \tau_1^2 + \frac{1}{2} G_z (4\tau_1^2 - \tau_1^2) \\ &= G_z \tau_1^2 \end{aligned} \quad (9)$$

the origin of the time axis at the isodelay point of the first RF pulse RF1 is thereby selected that coincides in good approximation with the middle of the RF pulse given SINC and rectangular pulses (thus symmetrical RF pulses).

At the point in time $t=2\tau_1+\tau_2$ of the stimulated echo S1, with the aid of Formula 8 the following first moment is again obtained:

$$m_1(2\tau_1) = -\int_0^{\tau_1} G_z \tilde{t} d\tilde{t} + \int_{\tau_1+\tau_2}^{2\tau_1+\tau_2} G_z \tilde{t} d\tilde{t} \qquad (10)$$

$$= -\frac{1}{2}G_z\tau_1^2 + \frac{1}{2}G_z[(2\tau_1+\tau_2)^2 - (\tau_1+\tau_2)^2] =$$

$$= G_z(\tau_1^2 + \tau_1\tau_2)$$

The first moment at the point in time of the first spin echo E1 and of the stimulated echo S1 are thus not equal to zero and differ from one another. If Equation 7 is considered again it is apparent that the first moment does not deliver any phase contribution to resting spin systems ($v_z=0$).

Therefore, the following hypothesis is the basis of the present invention: the cause of non-functionality of the known methods for transmitter adjustment during continuous feed of the patient bed is the additional phase that the spins accumulate as a result of the travel of the patient bed.

The problem of the adjustment method given continuous feed of the patient bed could thus simply be remedied in that no gradients are switched in the direction of the bed feed. However, this means a fundamental reworking of the adjustment method since the B1 curve of the transmission coil is also directionally dependent, for example.

Another possibility to remedy the problem is to replace the gradient scheme in the direction of the bed feed with such a scheme whose zeroth moment and first moment disappear at the point in time of the respective echo read out for the adjustment. This is possible via a reworking of the adjustment sequence according to the invention while maintaining the principle adjustment method.

A pulse sequence according to the invention that generates at least one echo signal from which an actual flip angle achieved with at least one RF pulse of the sequence can be determined given continuous travel of the examination subject, and includes a gradient scheme in the direction of the continuous travel of said examination subject, which gradient scheme is designed such that its first moment disappears at the points in time of each echo signal used for the determination of the flip angle.

Due to the disappearance of the 1st moment of the gradient scheme at the point in time of the echo, the accumulation of an unwanted phase of the spins as a result of the continuous travel is effectively suppressed, with which unwanted phase effects are avoided that can lead to a dephasing of the echo signals and whose subsequent computational correction can be impossible due to unknown field distributions.

The RF pulses of the pulse sequence can thereby be both selective and non-selective as well.

In a simple exemplary embodiment, the pulse sequence has at least three RF pulses which are radiated such that at least two and up to five echo signals can be generated. Such pulse sequences generate echo signals with which the actual flip angles of at least one RF pulse of the pulse sequence can be determined in a simple manner.

In an exemplary embodiment, the gradient scheme of the pulse sequence comprises crusher gradients to suppress unwanted signals in a direction perpendicular to the direction of the continuous travel of the examination subject.

A method according to the invention to determine the actual flip angle of at least one RF pulse of a pulse sequence which is achieved during a MR measurement (MR: magnetic resonance) under continuous travel of the examination subject through the measurement volume includes the steps:
execute the pulse sequence given continuous travel of the examination subject, wherein the pulse sequence comprises at least one RF pulse,
detect at least one echo signal of the MR sequence,
determine the flip angle actually achieved by at least one RF pulse of the pulse sequence based on the received echo signals,
wherein the gradient scheme of the MR sequence is designed in the travel direction of the examination subject such that the first moment disappears at the echo points in time of the acquired echoes.

As described with regard to the pulse sequence, the disappearance of the first moment of the gradient scheme in the direction of the movement of the examination subject at the point in time of the echoes avoids the accumulation of additional phase of the spins as a result of the travel, and therefore enables a robust determination of the flip angle.

The method according to the invention for adjustment of the transmitter voltage for RF pulses determines a reference transmitter voltage for a reference RF pulse from a flip angle determined according to the method described above given continuous travel of the examination subject through the measurement volume relative to a momentary position of the examination subject.

A magnetic resonance apparatus according the invention has a patient bed that can be moved continuously through the measurement volume of the magnetic resonance apparatus; a magnet; radio-frequency antennas to radiate RF pulses and receive echo signals; a gradient system comprising gradient coils and a pulse sequence control unit to control the gradient coils and radio-frequency antennas, wherein the pulse sequence control unit is designed in order to generate pulse sequences (described above) during the continuous travel of the patient bed; and with a computer that controls the individual system components of the magnetic resonance apparatus corresponding to a method described above.

The above object also is achieved in accordance with the present invention by a non-transitory, computer-readable data storage medium encoded with programming instructions that is loadable into a memory of a programmable computer of a magnetic resonance apparatus. The programming instructions cause the magnetic resonance apparatus to implement any or all of the embodiments of the method described above.

The advantages described with regard to the pulse sequence and the method to determine the actual flip angle of at least one RF pulse of a pulse sequence during an MR measurement under continuous travel of the examination subject through the measurement volume analogously also apply to the method according to the invention for adjustment of the transmitter voltage for RF pulses, the magnetic resonance apparatus according to the invention, and the non-transitory electronically readable data storage medium according to the invention.

DESCRIPTION OF THE PREFERRED EMBODIMENTS

Figure 1:
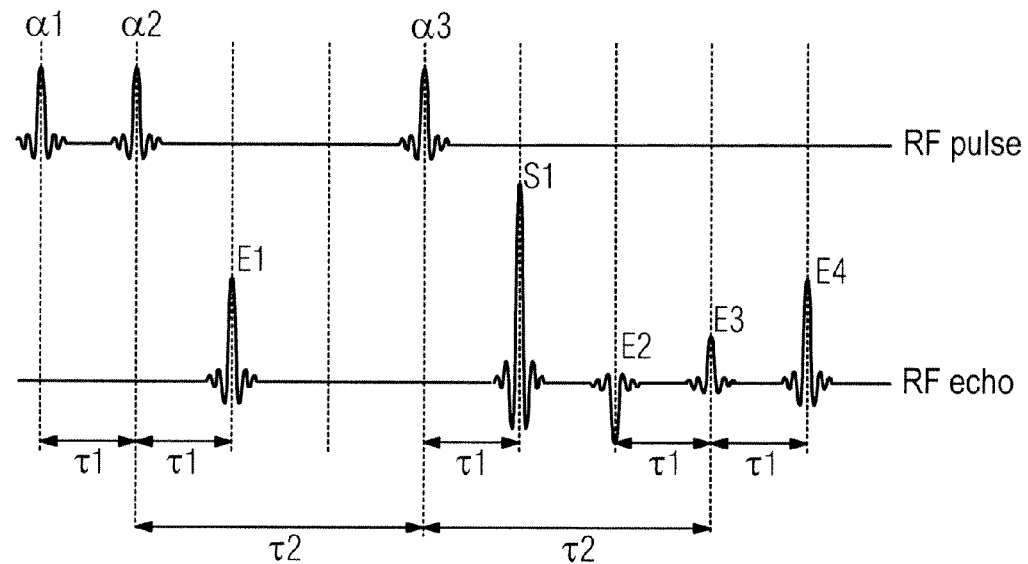
FIG. 1 is a schematic representation of a known sequence to generate up to five echo signals.

FIG. 1 shows a schematic representation of a known sequence to generate up to five echo signals. A first RF pulse with a flip angle $\alpha 1$ ($\alpha 1$ pulse) and a second RE pulse with a flip angle $\alpha 2$ ($\alpha 2$ pulse) are thereby radiated in a time interval $\tau 1$ in order to generate a spin echo signal E1 of the FID (FID: "free induction decay") of the first RF pulse at the point in time $2\tau 1$ after the first RF pulse ($\alpha 1$ pulse). After this, a third RE pulse with the flip angle $\alpha 3$ ($\alpha 3$ pulse) is radiated at a time $\tau 1+\tau 2$ after the $\alpha 1$ pulse.

Under the assumption $\tau 2 > 2*\tau 1$, the echo signals S1, E2, E3 and E4 respectively arise at the times $2*\tau 1+\tau 2$, $2*\tau 2$, $\tau 1+2*\tau 2$ and $2*(\tau 1+\tau 2)$. S1 is what is known as a stimulated echo. E2 is a spin echo that arises via refocusing of the echo E1 via the $\alpha 3$ pulse. E3 arises via the refocusing of the FID of the $\alpha 2$ pulse by the $\alpha 3$ pulse, and E4 arises via the refocusing of the FID of the $\alpha 1$ pulse by the $\alpha 3$ pulse.

Figure 2:
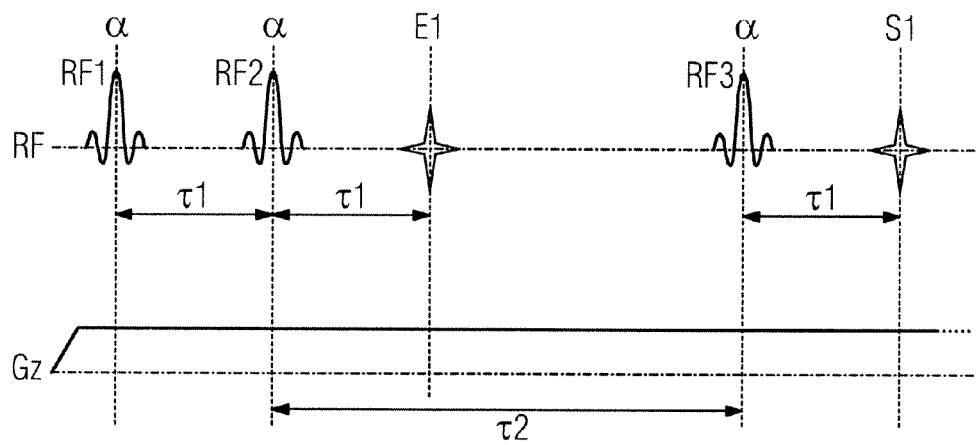
FIG. 2 shows a known pulse sequence as used by (for example) Meulen et al. (as described above) in order to determine the flip angle α achieved with a defined transmitter voltage.

FIG. 2 shows a known pulse sequence as described above (as it is used by Meulen et al., for example) in order to determine the flip angle $\alpha$ achieved with a defined transmitter voltage. In contrast to FIG. 1, here the RF pulses and the echo signals were indicated together in a common line (shown as upper line "RF") and in a second line of the associated gradient in the z-direction Gz.

Figure 3:
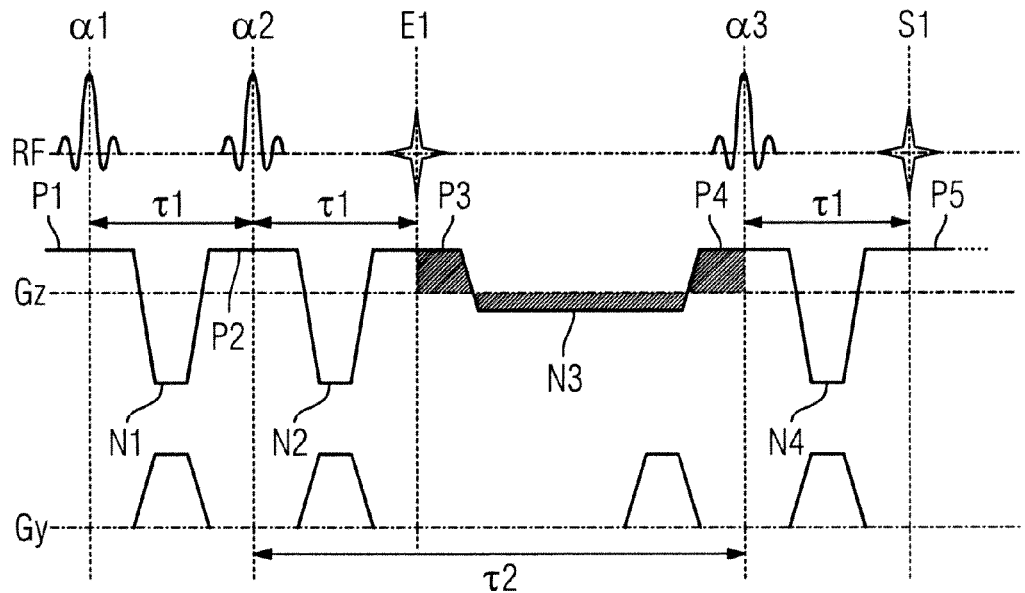
FIG. 3 shows, as an example, a sequence according to the invention for an exemplary embodiment of a determination method of the flip angle according to the invention.

FIG. 3 shows as an example a sequence according to the invention for a particularly elegant exemplary embodiment of a determination method of the flip angle according to the invention, which determination method uses a sequence composed of three RF pulses and which reads out the first spin echo E1 as well as the stimulated echo S1.

In contrast to the sequence shown in FIG. 2, here the gradient GZ in the direction of the bed feed advantageously comprises five trapezoidal gradients with positive amplitude P1, P2, P3, P4, P5, and four trapezoidal gradients with negative amplitude N1, N2, N3, N4.

The positive trapezoidal gradients that are switched in the direction of the continuous movement of the examination subject (here: z-direction) serve for slice selection during the RF radiation or, respectively, as a readout gradients of the echo signals to be read out. In the exemplary embodiment of FIG. 3, all positive gradients have the same flat top amplitude. The term "flat top" is used in MR engineering for the short upper base of a trapezoidal gradient and is also sometimes designated as a "plateau". The laterally rising and falling sides of the trapezoidal gradients are designated as "ramps".

The duration of the flat tops of the slice selection gradients of the second and third RF pulse $\alpha 2$ and $\alpha 3$ of the pulse sequence and the duration of the flat tops of the readout gradients of the echo E1 are of the same length in the embodiment shown in FIG. 3. The isodelay points of the RF pulses $\alpha 2$ and $\alpha 3$ temporally coincide with the middle of the flat tops of the respective slice selection gradients. The center of the echo E1 correspondingly coincides in time with the middle of the readout gradient P3. The duration of the flat top of the slice selection gradient of the first RF pulse $\alpha 1$ after the isodelay point in time of the first RF pulse is just as long as the duration of the flat top of the second RF pulse before its isodelay point. The duration of the flat top of the second readout gradient P5 up to the stimulated echo S1 likewise coincides with the duration of the flat top of the slice selection gradient P4 from the isodelay point of the third RF pulse $\alpha 3$ to the end of the flat top.

In the selected presentation here and in the following figures, the slice selection gradient of the first RF pulse $\alpha 1$ also coincides with that of the additional RF pulses. This is not necessary. A different form of slice selection gradient could also be relatively freely selected for the first RF pulse $\alpha 1$. It is likewise conceivable that none of the RF pulses of the pulse sequence has a slice selection gradient in the direction of the continuous travel of the examination subject. However, the condition of the disappearance of the first moment at the respective echo points in time used for the determination of the flip angle must be preserved in any case. In one exemplary embodiment (not shown), no gradient at all is switched in the direction of the continuous travel of the examination subject ($G_z=0$), which likewise satisfies the cited condition.

The trapezoidal gradients are therefore designed such that the time duration of the flat top of a slice selection gradient as of the isodelay point of the associated RF pulse ($\alpha 2$, for example) coincides with the time duration of an immediately following readout gradient up to the point in time of the associated echo (E1, for example). The time duration of the right ramp of the slice selection gradient is additionally chosen to be equal to the time duration of the left ramp of the immediately following readout gradient.

The time duration of the flat top of a readout gradient from the point in time of the associated echo (E1, for example) to the end of the flat top likewise coincides with the time duration of the flat top of an immediately following slice selection gradient up to the isodelay point in time of the associated RF pulse ($\alpha 3$, for example). The time duration of the right ramp of the readout gradient is additionally selected to be equal to the time duration of the left ramp of the immediately following slice selection gradient.

Furthermore in exemplary embodiments shown later with regard to FIGS. 5 and 6, the time duration of the flat top of a readout gradient as of the point in time of the associated echo (see for example S1, E2 and E3 in FIG. 5) can coincide with the time duration of the flat top of an immediately following readout gradient up to the point in time of the associated echo (for example E2, E3 and E4 in FIG. 5), wherein the time duration of the right ramp of the first of said readout gradient is equal to the time duration of the left ramp of the immediately following readout gradient.

By the selection of the gradient amplitudes, flat top durations and ramp times that was just described, 0th and 1st moment acquired from spins via the two adjacent, positive (half) gradients (also designated as "half positive neighboring gradients"; see below) can be compensated between immediately successive points in time from the group of isodelay points of RF pulses and echo points in time of echoes to be read out via a symmetrical, negative trapezoidal gradient whose center of symmetry lies temporally in the middle between the respective immediately successive isodelay points or, respectively, points in time of the echoes. The shown gradient scheme thus particularly elegantly satisfies the condition that the 1st moment of the gradient in the direction of the continuous travel of the examination subject disappears at the points in time of the acquired echo signals.

Further explanation with regard to FIG. 3: up until the last acquired echo (here the stimulated echo S1) a negative gradient N1, N2, N3, N4 follows each positive gradient P1, P2, P3, P4, P5, and vice versa. All positive gradients P1, P2, P3, E4, P5 have the same amplitude and flat top of identical length. The respective middle of a flat top of each positive gradient P1, P2, P3, P4, P5 coincides either with the isodelay point of one of the three RF pulses (given symmetrical RF pulses, the isodelay point corresponds to the center of symmetry of the RF pulse) or with one of the two echoes. The design of the negative gradients N1, N2, N3, N4 is symmetrical and such that the absolute value of the 0th moment is equal to the sum of the 0th moment (that is accumulated between the middle of the flat top of the left neighboring gradient and its end) and the moment that is acquired between the beginning of the right neighboring gradient and the middle of its flat top (also designated in the following as a "half positive neighboring gradient"). The 0th moment that is accumulated between the centers of two successive positive gradients is thus equal to zero.

In FIG. 3, this is represented as an example by the hatched areas of the gradients P3, N3 and P4 between the first spin echo E1 and the isodelay point in time of the third RF pulse α3 that satisfied this condition. This means that the absolute value of the sum of the hatched areas under P3 and P4 corresponds to the absolute value of the hatched area under N3, whereby these cancel each other out due to their opposite algebraic signs and the 0th moment accumulated over the entire hatched area (and in the other partial regions between the centers of two successive, positive gradients) adds up to zero.

The center of symmetry of each negative gradient N1, N2, N3, N4 also coincides with the center of gravity of the "half positive neighboring gradients" that were just defined. The gradient sub-scheme that is formed from two positive half gradients and the intervening negative gradient is therefore symmetrical.

It is thereby particularly elegantly achieved that the zeroth and first moment are zero, both at the respective isodelay points of the RF pulses α1, α2, α3 and at the respective points in time of the echoes E1 and S1.

For the zeroth moment this follows from the design itself, since the respective zeroth moments are compensated as described above. For the first moment this can be reproduced via direct integration with the aid of Equation 8. However, it also follows from the rule that the first moment of an asymmetrical gradient scheme can be calculated as if the entire zeroth moment were concentrated in the center of symmetry (see also Bernstein et al. J. Magn. Reson. Imaging 2: 583-588):

$$m_1 = m_0 \Delta t \text{ (symmetrical gradient scheme)} \qquad (11).$$

wherein $\Delta t$ is the time interval between the center of symmetry of the considered gradient scheme and the point in time at which the first moment $m_1$ is required.

If this rule is now successively applied to the symmetrical sub-scheme defined above (consisting of a negative gradient N1, N2, N3, N4 and the two adjacent half positive neighboring gradients) at the points in time (relative to the excitation RF pulse α1) τ1 (isodelay point of the second RF pulse α2), 2τ1 (point in time of the first spin echo E1), τ1+τ2 (isodelay point of the third RF pulse α3) and 2τ1+τ2 (point in time of the stimulated echo S1), $m_1 = 0$ respectively follows from Equation 11 since the 0th moment $m_0$ of the sub-scheme is respectively zero ($m_0 = 0$).

In the third line in FIG. 3, a gradient axis $G_y$ is furthermore indicated. The gradient pulses shown in the third line serves as what is known as a spoiler or gradient that dephases the FID of the second RF pulse α2 before the first spin echo E1 or, respectively, the FID of the third RF pulse α3 before the stimulated echo S1, such that the individual FIDs respectively deliver no signal contribution to the respective echo signals. The FID of the first RF pulse α1 is not dephased by means of a crusher gradient, since otherwise no echo materializes.

The direction of the gradient $G_y$ is thereby orthogonal to the direction of the travel direction of the bed (here: z-direction); otherwise it is arbitrary. The orthogonal condition ensures that no phase is acquired as a result of the travel.

The shown crusher gradients Gy are thereby only examples. The spoiler gradient shown to the left next to the third RF pulse α3 in FIG. 3 (third spoiler gradient from the left) could be (but does not need to be) omitted, for example, insofar as only the stimulated echo S1 is read out after the third RF pulse α3 since the spins whose signals later form the stimulated echo S1 are aligned longitudinally in the time interval between RF pulses α2 and α3. In this case it could even be advantageous to omit the third crusher gradients shown in FIG. 3, since the additional spin echoes E2, E3, E4 (see for example FIG. 1) after the third RF pulse α3 are thereby suppressed, and thus the time τ2 can be selected to be shorter without it leading to an interference between the additional echoes E2, E3, E4 and the stimulated echo S1.

Figure 4:
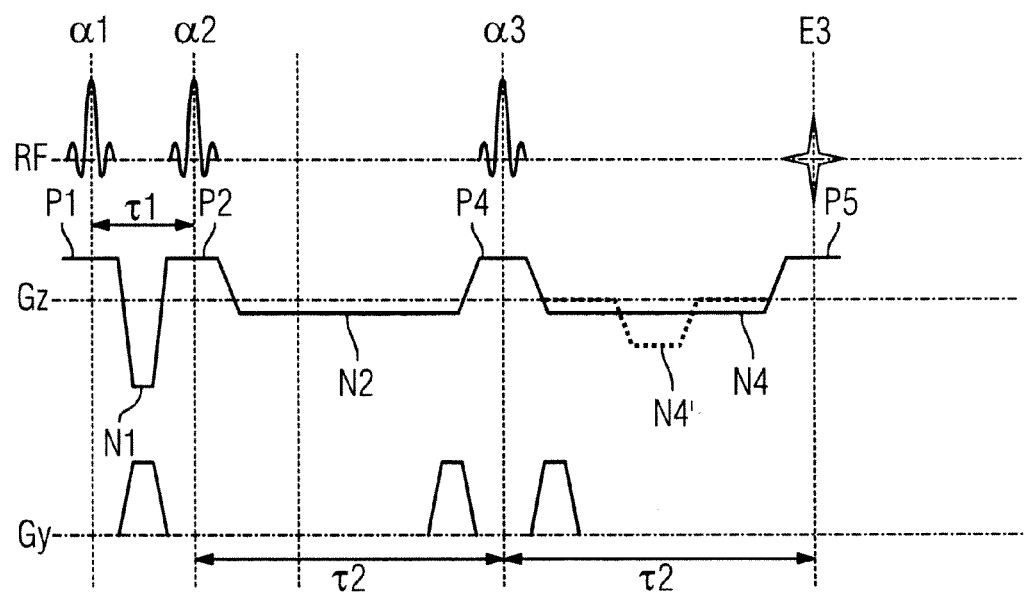
FIG. 4 shows, as an example, an additional sequence according to the invention for an exemplary embodiment of a determination method of the flip angle according to the invention.

FIG. 4 shows as an example an additional sequence according to the invention for an additional, particularly elegant exemplary embodiment of a determination method of the flip angle according to the invention which uses a sequence made up of three RF pulses (see also FIG. 1) and which reads out the third spin echo E3 generated by the RF pulses α2 and α3.

As was already indicated above with reference to the publication by Perman et al., 90° and 180° RF pulses can be determined with the aid of the third spin echo E3 that arises via the refocusing of the FID of the second RF pulse α2 by the third RF pulse α3 at the point in time $\tau_2$ after the third RF pulse α3. In order to read out the third spin echo E3 instead of the stimulated echo S1 (as in FIG. 3) according to the invention, in comparison to FIG. 3 the fifth positive trapezoidal gradient P5 must be shifted forward in time by $\tau_2 - \tau_1$, and the center of symmetry of the fourth negative gradient N4 must be shifted to the point in time $\tau_2/2$ after the third RF pulse α3. The readout gradient P3 of the first spin echo E1 and the negative gradient N3 following this can be omitted in an adaptation of the scheme to the read-out echo E3 under the condition of the disappearance of the first moment.

The amplitude of the negative gradients N2 and N4 can be reduced relative to the negative gradients according to FIG. 3, and therefore their temporal length can be increased insofar as this takes place in such a manner that the 0th moment does not change. This is outlined in FIG. 4 with regard to the negative gradient N4; one time the gradient is drawn as a dotted curve N4' according to FIG. 3 and one time as a continuously drawn curve N4 with reduced amplitude and increased time duration.

Here as well, suitable crusher gradients can be switched in a direction perpendicular to the direction of the continuous travel of the examination subject. The shown crusher gradients are only one possible example.

Figure 5:
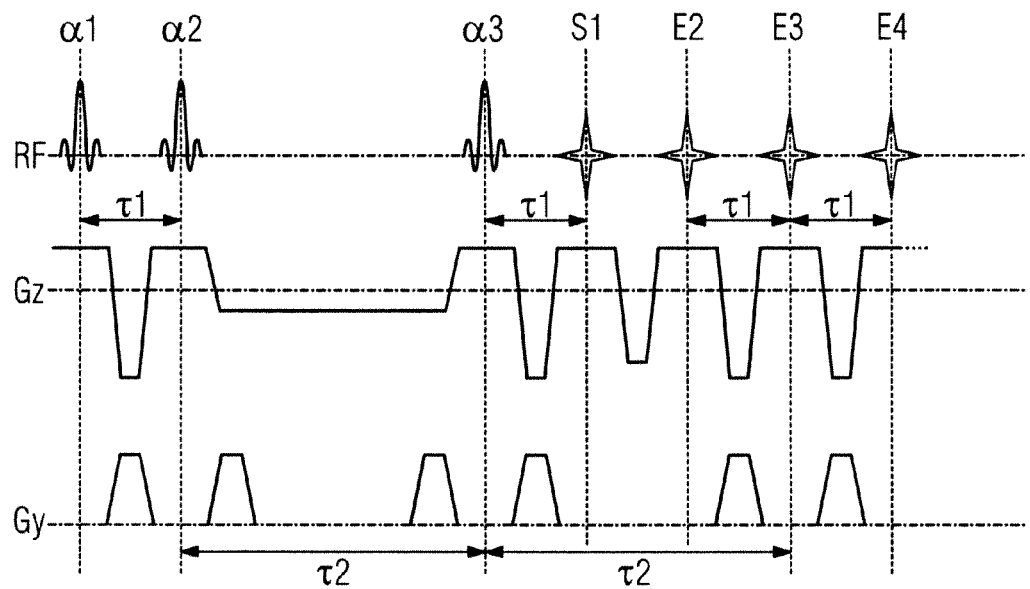
FIG. 5 shows, as an example, an additional sequence according to the invention for an exemplary embodiment of a determination method of the flip angle according to the invention.

FIG. 5 shows an example of an additional sequence according to the invention for an additional exemplary embodiment of a determination method of the flip angle according to the invention, which method uses a sequence of three RF pulses, and which method reads out the echoes S1, E2, E3 and E4 generated after the third RF pulse α3, which echoes are generated by at least two of the RF pulses α1, α2 and α3.

As was indicated above with reference to the publication by Carlson et al., the flip angle achieved with the RF pulses can be determined with the aid of the stimulated echo S1 at the point in time $\tau_1$ after the third RF pulse α3 and the following spin echoes E2 at the point in time $\tau_2-\tau_1$ after the third RF pulse α3, E3 at the point in time $\tau_2$ after the third RF pulse α3 and E4 at the point in time $\tau_2+\tau_1$ after the third RF pulse α3.

For the method according to the invention, the gradient switching in the z-direction (direction in which the examination subject is moved) must again be adapted according to the invention (see conditions as indicated with regard to FIG. 3). For this purpose, for example, in comparison to FIG. 3 three additional positive readout gradients must be appended (for example in turn with the same amplitude and flat top duration as the readout gradients that are already present) whose center of symmetry coincides temporally with the respective echo. As in the case of FIG. 4, the positive readout gradient P3 of the first spin echo E1 and the following negative gradient N3 can be omitted since the first spin echo E1 is not read out in this exemplary embodiment.

To compensate the 0th and 1st moment that is accumulated between two echoes, respective symmetrical negative gradients whose center of symmetry respectively coincides with the temporal middle of two successive echoes (more precisely: with their respective echo points in time) are added between the positive gradients. For the echoes S1 and E2, E2 and E3 and E3 and E4, this corresponds to the times $\tau_1+(\tau_2-2\tau_1)/2=\tau_2/2$, $(\tau_2-\tau_1)+\tau_1/2=\tau_2-\tau_1/2$, or, respectively, $(\tau_2+(\tau_2+\tau_1))/2=\tau_2+\tau_1/2$, respectively after the third RF pulse α3. The area of each negative gradient is thereby provided by the sum of the area of the left half (positive) neighboring gradient from the echo middle (corresponding to the echo point in time of the leading echo) to the end, and the area of the right half (positive) neighboring gradient from the start up to the echo middle (corresponding to the echo point in time of the trailing echo).

Here corresponding crusher gradients are also switched in a direction perpendicular to the z-direction (here in the y-direction) in order to dephase the FID of the third RF pulse or, respectively, of the second RF pulse. The shown crusher gradients are hereby only one example from multiple possibilities.

Figure 6:
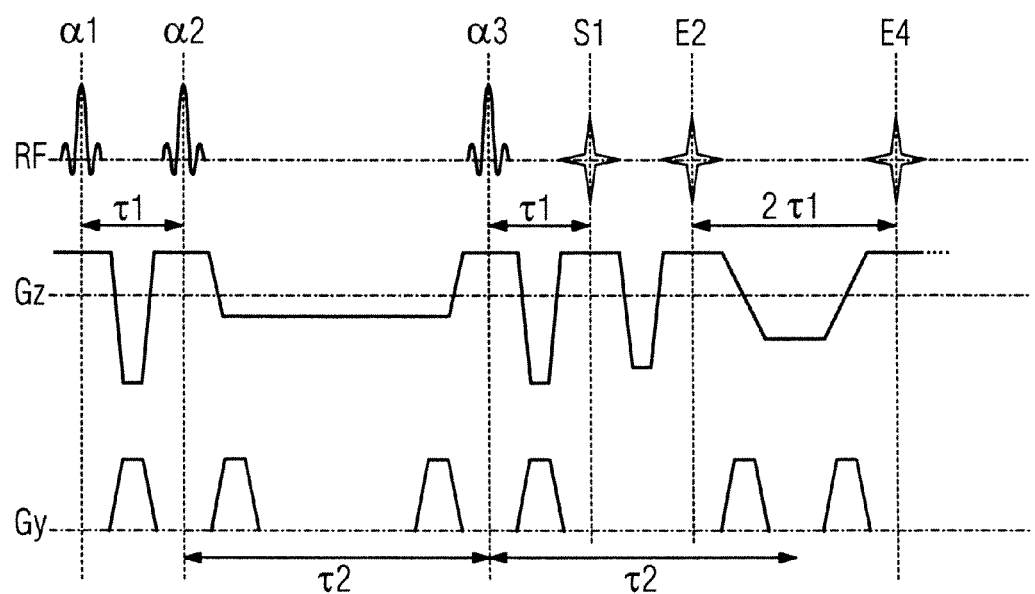
FIG. 6 shows, as an example, an additional sequence according to the invention for an exemplary embodiment of a determination method of the flip angle according to the invention.

FIG. 6 shows as an example an additional sequence according to the invention for a modification of the last exemplary embodiment of a determination method of the flip angle according to the invention, which determination method uses a sequence of three RF pulses and which reads out the echoes S1, E2 and E4—but not E3—that arise after the third RF pulse α3, generated by the RF pulses α1, α2 and α3, as is proposed in the aforementioned article by Carlson et al. on Page 440, penultimate Paragraph.

In the z-direction—thus the direction in which the examination subject is moved—the gradients are again arranged such that a positive gradient of the same amplitude and the same duration of the respective flat top is switched at each RF pulse α1, α2 and α3, and at each read-out echo S1, E2, E4, and such that a negative gradient is respectively switched between these positive gradients, such that the 0th moment disappears between the middles of two successive positive gradients, and such that gradient subscheme composed of the two half positive gradients and the negative gradient is mirror symmetric with respect to the middles of the two successive positive gradients.

In a direction perpendicular to the z-direction (here in the y-direction), corresponding crusher gradients are also switched here that dephase the otherwise interfering signals. The shown crusher gradients are again only examples.

Figure 7:
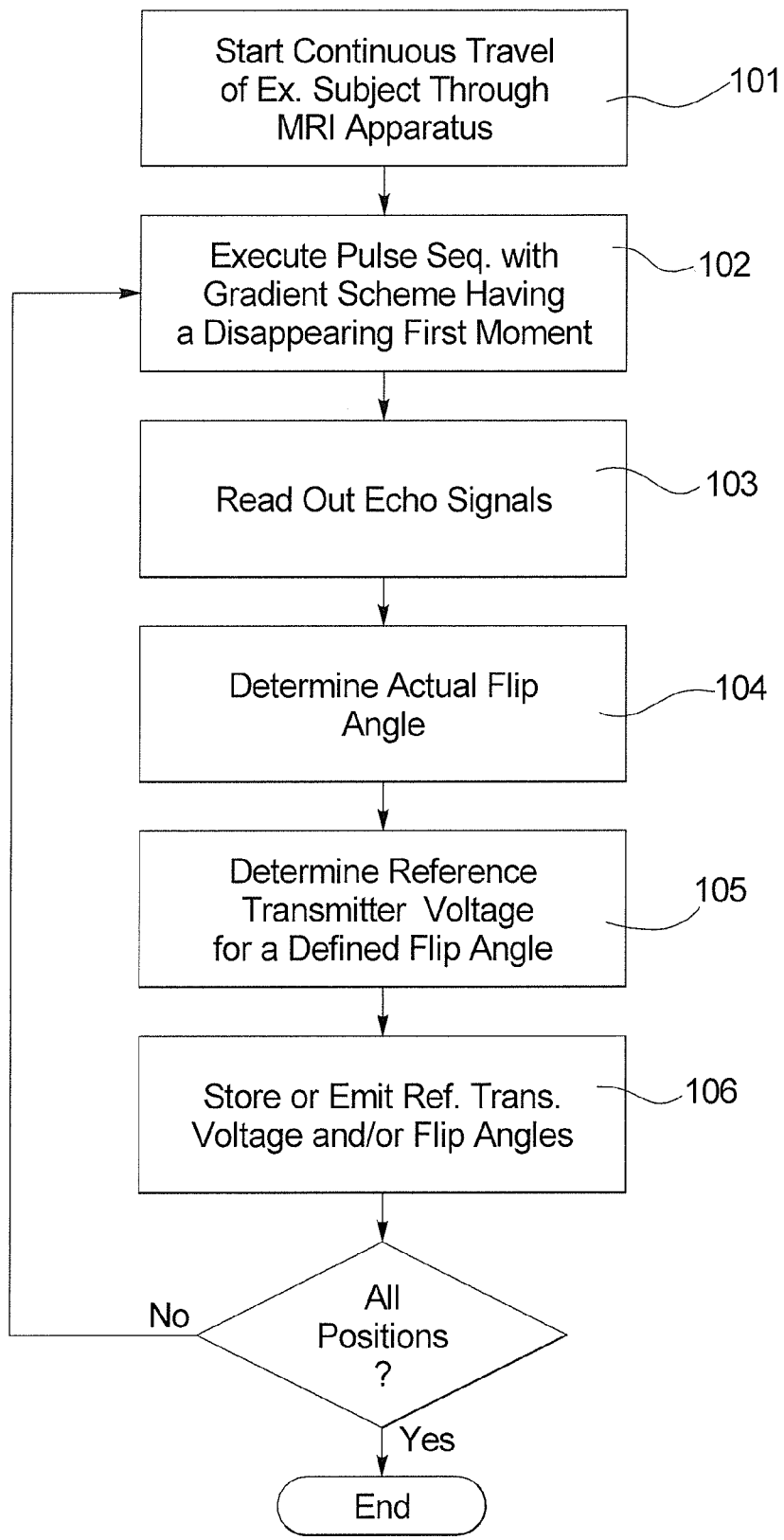
FIG. 7 is a schematic workflow diagram for an embodiment of the method according to the invention.

FIG. 7 shows a schematic workflow diagram regarding the method according to the invention. A continuous travel of an examination subject through a magnetic resonance apparatus is started (Block 101). For example in that a patient bed with an examination subject located thereupon is moved continuously through the measurement volume of the magnetic resonance apparatus.

During the continuous travel of the examination subject, a pulse sequence is executed that generates at least one echo signal from which an actual flip angle achieved with at least one RF pulse of the sequence can be determined, and whose gradient scheme is designed in the direction of the continuous travel such that its first moment disappears at the points in time of each echo signal used to determine the flip angle (Block 102).

Those echo signals generated with the sequence are read out (Block 103) that are used in Block 104 for the determination of the actual flip angle.

Furthermore, a reference transmitter voltage with which a reference RF pulse achieves a defined flip angle (for example 90° or 180°) at the observed position of the examination subject can be determined from the defined flip angle in a known manner (Block 105). Based on this information, the transmitter voltage can also be adjusted in a known manner for other flip angles or RF pulses with other envelope B1 field in later examinations of the examination subject at the same position.

The determined reference transmitter voltages or likewise the actual measured flip angle can furthermore be stored together with the associated position and/or be output to a display device, for example a control panel (Block 106).

Steps 101 through 105 are repeated until all positions of interest of the examination subject within the magnetic resonance apparatus have been reached or until the continuous travel can no longer be continued since (for example) the patient bed has reached its maximum travel position. In the latter case, the methods ends ("end").

The embodiment of the pulse sequence and the determination of the at least one flip angle can in particular already be started directly after the positioning of the examination subject on the patient bed, for example while the patient bed is moved to the first examination position of the examination subject, and flip angles or, respectively, reference transmitter voltages can be determined and/or stored for all "potential" examination positions crossed during this travel. If an examination actually takes place later in proximity to one of these positions, the stored values are read and used to calculate the actual output voltage of the radio-frequency amplifier. It is thereby possible to average between multiple "node points" adjacent to the actual bed position for the adjustment results present in the form of flip angles or reference transmitter voltages. The time for the adjustment measurements that are otherwise to be implemented separately is thereby saved, and the examination duration is accordingly shortened. The costs for the examination and the stress to which the patient is exposed due to the examination are reduced with the examination duration. For example, if the positioning of the patient takes place such that he is driven head first into the magnet, and if the individual examination positions are executed beginning by the head in the direction of the feed, all adjustment measurements necessary for the examination can thus be determined in the initial travel. This is particularly of interest when the examination comprises a large number of different bed positions. A particularly large number of different bed positions occur, for example, in what are known as whole-body examinations and in what is known as isocenter screening. In the latter, it is sought to achieve optimal image quality via placement of the currently measured slice stack (or, respectively, the actual measured slice) in the isocenter of the magnet. Furthermore, given use of MR systems with a short extent in the z-direction ("short bore system") that increase the patient comfort and make it possible to examine claustrophobic patients, the number of different bed positions is normally increased relative to a corresponding examination in a conventional MR system.

Figure 9:
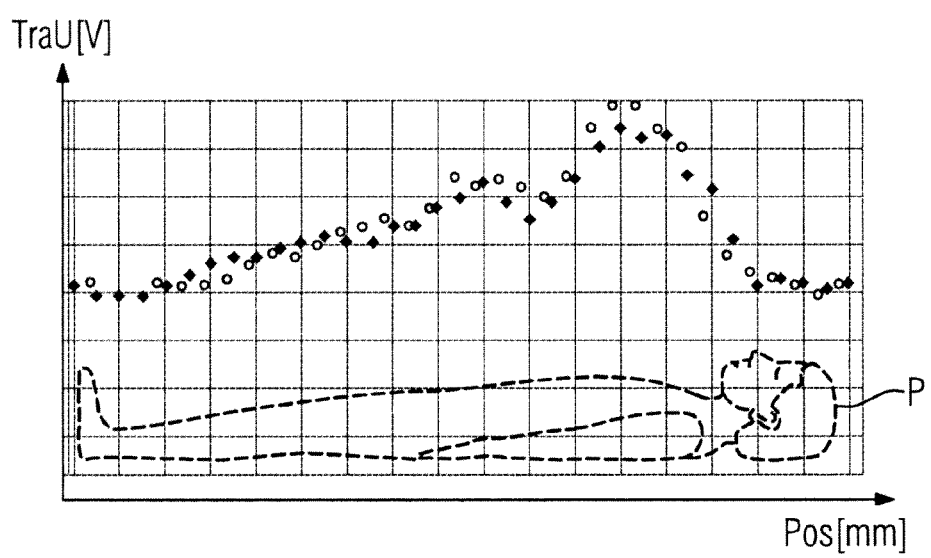
FIG. 9 shows an example of adjustment values achieved with a method according to the invention.

FIG. 9 shows a comparison of values determined for reference transmitter voltage "TraU" (diamonds) by means of a method according to the invention according to FIG. 3 during continuous feed of the patient bed at 50 mm/s with values (circles) determined iteratively while stationary according to the prior art, depending on the position "Pos" at which measurements were performed in a patient P. The transmitter reference voltage "TraU" is hereby the transmitter voltage that is required in order to realize a 180° pulse with a rectangular reference RF pulse with a duration of one millisecond. Although the determination of the reference transmitter voltage is not implemented iteratively according to the method according to the invention, the results are in good agreement.

Figure 8:
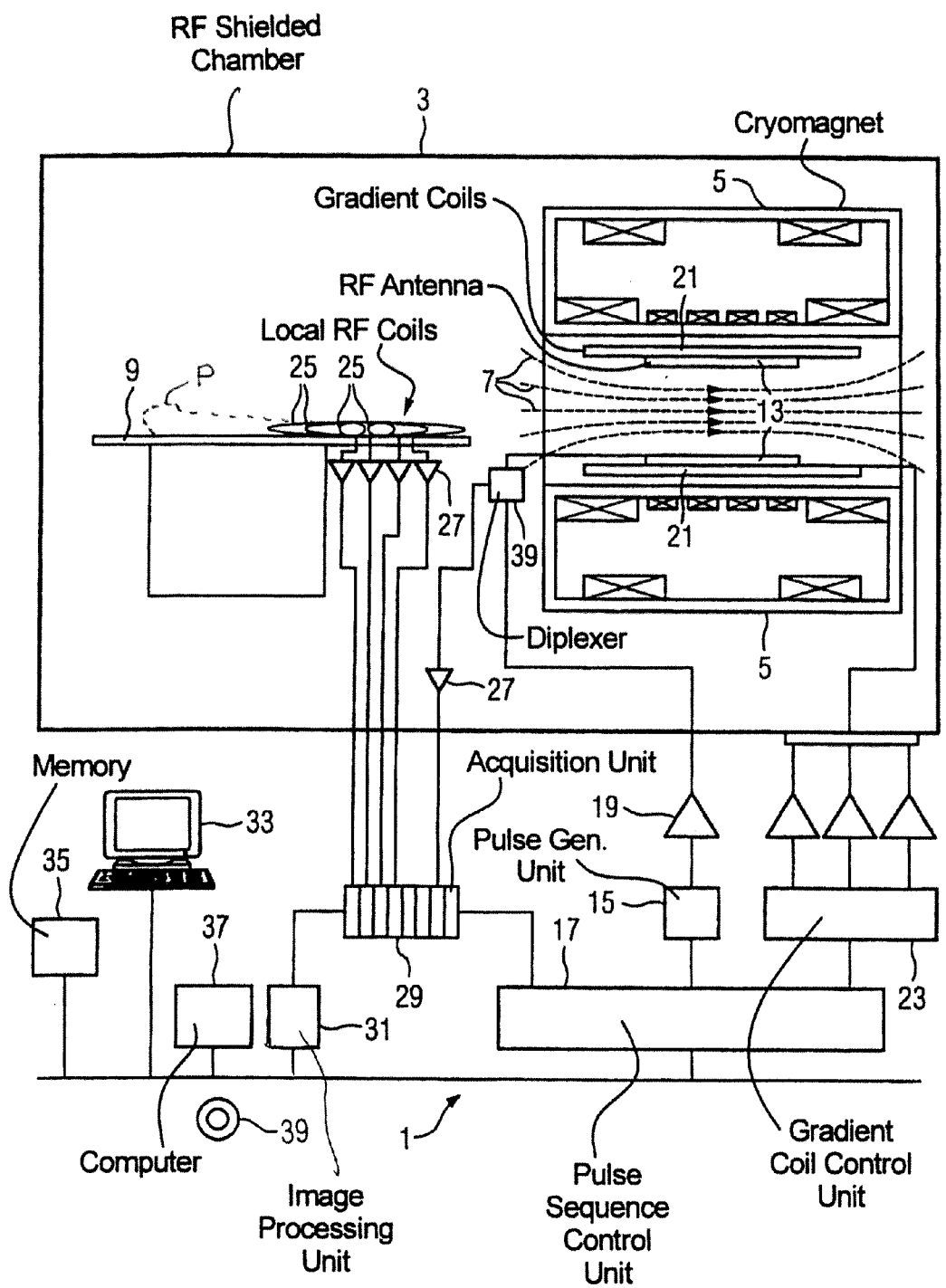
FIG. 8 schematically illustrates a magnetic resonance apparatus with which the methods according to the invention are implemented.

FIG. 8 schematically shows the design of a magnetic resonance apparatus 1 with its significant components. In order to examine a body by means of magnetic resonance imaging, various magnetic fields tuned as precisely as possible to one another in terms of their temporal and spatial characteristics are radiated towards the body.

A strong magnet—typically a cryomagnet 5 with a tunnel-shaped opening—arranged in a radio frequency-shielded measurement chamber 3 generates a static, strong basic magnetic field 7 that typically amounts to 0.2 Tesla to 7 Tesla or more. An examination subject, a body or a body part to be examined (here represented as a patient P) is borne on a patient bed 9 that can be moved continuously through the measurement volume of the magnetic resonance apparatus and is driven in the homogeneous region of the basic magnetic field 7 (measurement volume).

The excitation of the nuclear spins of the body takes place via magnetic radio-frequency pulses (RF pulses) that are radiated via a radio-frequency antenna (shown here as a body coil 13). The radio-frequency excitation pulses are generated by a pulse generation unit 15 that is controlled by a pulse sequence control unit 17. After an amplification by a radio-frequency amplifier 19, they are directed to the radio-frequency antenna. The radio-frequency system shown here is merely schematically indicated. Typically, more than one pulse generation unit 15, more than one radio-frequency amplifier 19 and multiple radio-frequency antennas are used in a magnetic resonance apparatus 1.

Furthermore, the magnetic resonance apparatus 1 possesses gradient coils 21 with which magnetic gradient fields are switched during a measurement, for example for selective slice excitation and for spatial coding of the measurement signal. The gradient coils 21 are controlled by a gradient coil control unit 23 that—like the pulse generation unit 15—is connected with the pulse sequence control unit 17. The pulse sequence control unit 17 is designed such that a pulse sequence according to the invention can be generated.

The signals emitted by the excited nuclear spins are received by the body coil 13 and/or by local coils 25, amplified by associated radio-frequency preamplifiers 27, and additionally processed and digitized by a receiver unit 29.

Given a coil that can be operated both in transmission mode and in reception mode—for example the body coil 13—the correct signal routing is regulated by a transmission/reception duplexer 39.

An image processing unit 31 generates from the measurement data an image that is presented to a user via a control console 33 or is stored in a memory unit 35. A central computer 37 controls the individual system components, in particular during the acquisition of the measurement data. The central computer 37 is designed such that a movement of the patient bed 9 and pulse sequences according to the present invention can be implemented, and a method according to the invention is implementable. For example, for this a computer program product according to the invention is loaded on or included in the computer 37 so as to be executable. The computer program product can be stored on an electronically readable data medium—a DVD 39, for example—so that this computer program product can then be read from the DVD 39 by the central computer 37 and be executed.

Although modifications and changes may be suggested by those skilled in the art, it is the intention of the inventor to embody within the patent warranted hereon all changes and modifications as reasonably and properly come within the scope of his contribution to the art.

I claim as my invention:
1. A method for operating a magnetic resonance system, comprising:
from a control computer, operating a magnetic resonance data scanner comprising a radio-frequency (RF) antenna arrangement and a gradient coil system to execute a pulse sequence that includes radiating at least one RF pulse from said RF antenna arrangement into an examination subject while said examination subject is continuously moving through the magnetic resonance data acquisition scanner in a direction of continuous travel, said at least one RF pulse giving nuclear spins in the examination subject a flip angle that causes the nuclear spins to emit at least one echo signal;
from said control computer, in said pulse sequence, also operating said gradient coil system to activate gradient magnetic fields in said magnetic resonance data acquisition scanner according to a gradient scheme that occurs in said pulse sequence between said at least one RF pulse and each echo signal caused thereby, and, in said control computer, configuring said gradient scheme with respect to said direction of said continuous travel to cause a first moment of said gradient scheme in the direction of said continuous travel to disappear at a point in time of each of said at least one echo signal;

in said control computer, analyzing said at least one echo signal, obtained after activating the configured gradient scheme, to determine an actual value of said flip angle; and storing the actual value of the flip angle in a memory accessible by said control computer and making the stored actual value of the flip angle available from the memory, via the control computer, in electronic form for subsequent operation of said magnetic resonance data scanner to acquire magnetic resonance data from the examination subject.

2. A method as claimed in claim 1 comprising from said control computer operating said gradient coil system to switch spoiler gradients in said gradient scheme that suppress unwanted signals in a direction perpendicular to said direction of continuous travel.

3. A method as claimed in claim 1 comprising, from said control computer operating said RF antenna arrangement in said pulse sequence to radiate at least three RF pulses and thereby producing at least two echo signals.

4. A method as claimed in claim 3 comprising from said control computer, operating said magnetic resonance data acquisition scanner to acquire said magnetic resonance data by operating said gradient coil system to read out said echo signals under a readout gradient in said direction of continuous travel and to switch a slice selection gradient in said direction of continuous travel for at least one of said three RF pulses selected from the group consisting of a second of said at least three RF pulses and a third of said at least three RF pulses in said gradient scheme in a direction of said continuous travel.

5. A method as claimed in claim 4 comprising, from said control computer, operating said gradient coil system in said pulse sequence by switching a combination of gradient pulses in said pulse sequence as respective trapezoidal gradients with a same amplitude, said combination of gradient pulses being selected from the group consisting of a slice selection gradient for an RF pulse and a readout gradient for an echo signal immediately following said RF pulse, a readout gradient for an echo signal and a slice selection gradient for an RF pulse immediately following said echo signal, and respective readout gradients for two echo signals in immediate succession.

6. A method as claimed in claim 5 comprising configuring said gradient scheme in said control computer to give flat tops of respective slice selection gradients for a second and a third of said RF pulses in said pulse sequence, and flat tops of readout gradients for at least one echo signal read out before a last echo signal, of equal length.

7. A method as claimed in claim 5 comprising, in said control computer configuring said trapezoidal gradients in said gradient scheme such that the time duration of the flat top of a slice selection gradient from an isodelay point of the associated RF pulse to the end of the flat top coincides with the time duration of the flat top of an immediately following readout gradient up to a point in time of the associated echo, wherein the time duration of the right ramp of the slice selection gradient is equal to the time duration of the left ramp of the immediately following readout gradient and/or the time duration of the flat top of a readout gradient from the start of the flat top to the point in time of the associated echo coincides with the time duration of the flat top of an immediately following slice selection gradient up to the isodelay point of the associated RF pulse, wherein the time duration of the right ramp of the readout gradient is equal to the time duration of the left ramp of the immediately following slice selection gradient, and/or the time duration of the flat top of a readout gradient from the associated echo to the end of the flat top coincides with the time duration of the flat top of an immediately following readout gradient up to the point in time of the associated echo, wherein the time duration of the right ramp of the first of said readout gradients is equal to the time duration of the left ramp of the second of said readout gradients, wherein the respective 0th and 1st moment acquired from spins via these two (adjacent half) gradients between immediately successive points in time from the group of isodelay points of RF pulses associated with respective slice selection gradients and echo points in time of echoes to be read out is compensated via a symmetrical trapezoidal gradient whose center of symmetry lies in the middle between the respective immediately successive isodelay points in time or, respectively, points in time of the echoes.

8. A method as claimed in claim 1 comprising, from said control computer, operating said gradient coil system in said pulse sequence by switching no gradient in the direction of continuous travel of the examination subject.

9. A method as claimed in claim 1 comprising said at least one RF pulse from an RF transmitter, of said RF coil arrangement, operating according to a transmitter voltage, and determining a reference transmitter voltage for a reference RF pulse from said determined flip angle, relative to a current position of the examination subject in said continuous travel.

10. A method as claimed in claim 9 comprising, after positioning the examination subject on the patient bed, moving the patient bed to a first examination position in said magnetic resonance data acquisition scanner and determining said reference transmitter voltage for each successive position occupied by said patient bed and said patient during said continuous travel.

11. A magnetic resonance apparatus comprising:
a magnetic resonance data acquisition scanner comprising a patient table that is movable through said data acquisition unit and that is configured to receive an examination subject therein, and said scanner comprising a radio-frequency (RF) antenna arrangement and a gradient coil system;
a control computer configured to operate said magnetic resonance data acquisition scanner to execute a pulse sequence that includes radiating at least one RF pulse from said RF antenna arrangement into an examination subject while continuously moving said examination subject on the patient table through the magnetic resonance data acquisition scanner in a direction of continuous travel, said at least one RF pulse giving nuclear spins in the examination subject a flip angle that causes the nuclear spins to emit at least one echo signal;
said control computer being configured to operate said gradient coil system of said data acquisition scanner in said phase sequence to activate gradient magnetic fields in said magnetic resonance data acquisition scanner according to a gradient scheme that occurs in said pulse sequence between the at least one RF pulse and each echo signal caused thereby, said control computer being configured to configure said gradient scheme with respect to said direction of said continuous travel to cause a first moment of said gradient scheme in the direction of said continuous travel to disappear at a point in time of each of said at least one echo signal;
said control computer being configured to analyze said at least one echo signal, obtained after activating the configured gradient scheme, to determine an actual value of said flip angle;

a memory accessible by said control computer; and said control computer being configured to store the actual value of the flip angle in said memory and to make the stored actual value of the flip angle available from the memory, via the control computer, in electronic form for subsequent operation of said magnetic resonance data scanner to acquire magnetic resonance data from the examination subject.

12. A non-transitory, computer-readable data storage medium encoded with programming instructions, said data storage medium being loadable into a control unit of magnetic resonance apparatus comprising a data acquisition scanner with a continuously moving patient table, and said scanner comprising a radio-frequency (RF) antenna arrangement and a gradient coil system, said programming instructions causing said control computer to:

operate the magnetic resonance data acquisition scanner to execute a pulse sequence that includes radiating at least one RF pulse from said RF antenna arrangement into an examination subject while continuously moving said examination subject on the patient table through the magnetic resonance data acquisition scanner in a direction of continuous travel, said at least one RF pulse giving nuclear spins in said examination subject a flip angle that causes the nuclear spins to emit at least one echo signal;

operate said data acquisition scanner to activate gradient magnetic fields in said magnetic resonance data acquisition scanner according to a gradient scheme that occurs in said pulse sequence between the at least one RF pulse and each echo signal caused thereby, and to configure said gradient scheme with respect to said direction of said continuous travel to cause a first moment of said gradient scheme in the direction of said continuous travel to disappear at a point in time of each of said at least one echo signal;

analyze said at least one echo signal, obtained after activating the configured gradient scheme, to determine an actual value of said flip angle; and store the actual value of the flip angle in a memory accessible by said control computer and make the stored actual value of the flip angle available from the memory, via the control computer, in electronic form for subsequent operation of said magnetic resonance data scanner to acquire magnetic resonance data from the examination subject.

* * * * *